(12) United States Patent
Tucker

(10) Patent No.: US 10,398,586 B2
(45) Date of Patent: Sep. 3, 2019

(54) APPARATUS FOR TREATING ERECTILE DYSFUNCTION AND ENHANCING PENILE ENLARGEMENT

(71) Applicant: Jerry L. Tucker, Hendersonville, NC (US)

(72) Inventor: Jerry L. Tucker, Hendersonville, NC (US)

( * ) Notice: Subject to any disclaimer, the term of this patent is extended or adjusted under 35 U.S.C. 154(b) by 166 days.

(21) Appl. No.: 15/680,726

(22) Filed: Aug. 18, 2017

(65) Prior Publication Data

US 2018/0055678 A1 Mar. 1, 2018

Related U.S. Application Data

(60) Provisional application No. 62/378,790, filed on Aug. 24, 2016.

(51) Int. Cl.
*A61F 5/00* (2006.01)
*A61F 5/41* (2006.01)

(52) U.S. Cl.
CPC .......... *A61F 5/41* (2013.01); *A61F 2005/414* (2013.01)

(58) Field of Classification Search
CPC .............................. A61F 5/41; A61F 2005/414
USPC ...................................................... 600/38–41
See application file for complete search history.

(56) References Cited

U.S. PATENT DOCUMENTS

| | | | | |
|---|---|---|---|---|
| 5,306,227 A | * | 4/1994 | Osbon | A61F 5/41 600/41 |
| 5,810,710 A | * | 9/1998 | Burgos | A61F 5/41 600/38 |
| 6,659,938 B1 | * | 12/2003 | Orlowski | A61F 5/41 600/38 |
| 9,308,117 B2 | * | 4/2016 | Oh | A61F 5/41 |
| 2002/0137983 A1 | * | 9/2002 | Chen | A61F 5/41 600/41 |

* cited by examiner

*Primary Examiner* — John P Lacyk
(74) *Attorney, Agent, or Firm* — Chambliss, Bahner & Stophel, P.C.

(57) ABSTRACT

An apparatus for enhancing erection of a penis includes an expandable first member that partially encircles an upper portion of the penis and partially constricts at least a first vein of the penis to reduce the volume of blood carried away from the penis via the first vein. A second member is mounted to the first member includes left and right shoulder sections configured to contact the penis shaft along the left and right sides the urethra. A contoured section is formed between and extends outwards away from the shoulders so that, when the shoulder sections contact the penis shaft and the first member encircles at least partially encircles the upper portion of the penis, the contoured section extends over and does not constrict the urethra.

20 Claims, 5 Drawing Sheets

APPARATUS FOR TREATING ERECTILE DYSFUNCTION AND ENHANCING PENILE ENLARGEMENT

CROSS-REFERENCE TO RELATED APPLICATIONS

This application claims the benefit of U.S. Provisional Application No. 62/378,790, filed Aug. 24, 2016 and entitled "Apparatus for Treating Erectile Dysfunction and Enhancing Penile Enlargement," the disclosure of which is incorporated by reference herein in its entirety.

FIELD OF THE INVENTION

This invention relates to the field of medical and enhancement devices for assisting in achieving and sustaining erection of a penile organ. More particularly, this invention relates to a device for treating erectile dysfunction and enhancing penile enlargement.

BACKGROUND

Erectile dysfunction (ED) is an ailment that impacts or inhibits a male's ability to achieve or sustain an erection of the penile organ for satisfactory sexual activity. ED may vary in severity. While some men have a total inability to achieve the erection, others have an inconsistent ability to achieve the erection or may sustain only brief erections. Over time, a variety of treatment options have been developed and are now available for men with ED. Among others, these treatment options include drugs that are administered orally, drugs that are administered directly into the penile organ, mechanical aids such as constriction rings and vacuum pumps, and surgical implants such as semi-rigid penile prosthesis, inflatable penile prosthesis, etc. Each treatment method has its own advantages and disadvantages. In addition to being used by men for treating ED, the above-described drugs and mechanical devices may also be used by men without ED who are seeking more enhanced erections. Externally-applied mechanical devices used to treat ED, such as constriction rings, may be unsafe, cause uncomfortable erections or impair ejaculation.

What is needed, therefore, is an improved method and apparatus for treating erectile dysfunction and that enhances penile enlargement.

SUMMARY

The above and other needs are met by a prosthetic apparatus for enhancing penile erection of a penis, where the penis includes a shaft with an upper portion and a lower portion, a urethra extending lengthwise along the lower portion of the shaft, and a first vein for carrying blood away from the penis located on top of the upper portion. The apparatus includes an expandable first member configured to at least partially encircle the upper portion of the penis and to partially constrict the first vein to reduce the volume of blood carried away from the penis via the first vein in order to enhance erection of the penis. The apparatus further includes a rigid or semi-rigid second member mounted to the first member and configured to contact a lower portion of the penis. The second member includes left and right shoulder sections configured to contact the penis shaft along the left and right sides the urethra. A contoured section is formed between and extends downwards so that, when the shoulder sections contact the bottom of the penis shaft and the first member encircles the upper portion of the penis, the contoured section extends around without constricting the urethra.

BRIEF DESCRIPTION OF THE DRAWINGS

Further advantages of the invention are apparent by reference to the detailed description when considered in conjunction with the figures, which are not drawn to scale so as to more clearly show the details, wherein like reference numbers indicate like elements throughout the several views, and wherein.

DETAILED DESCRIPTION

Figure 1:
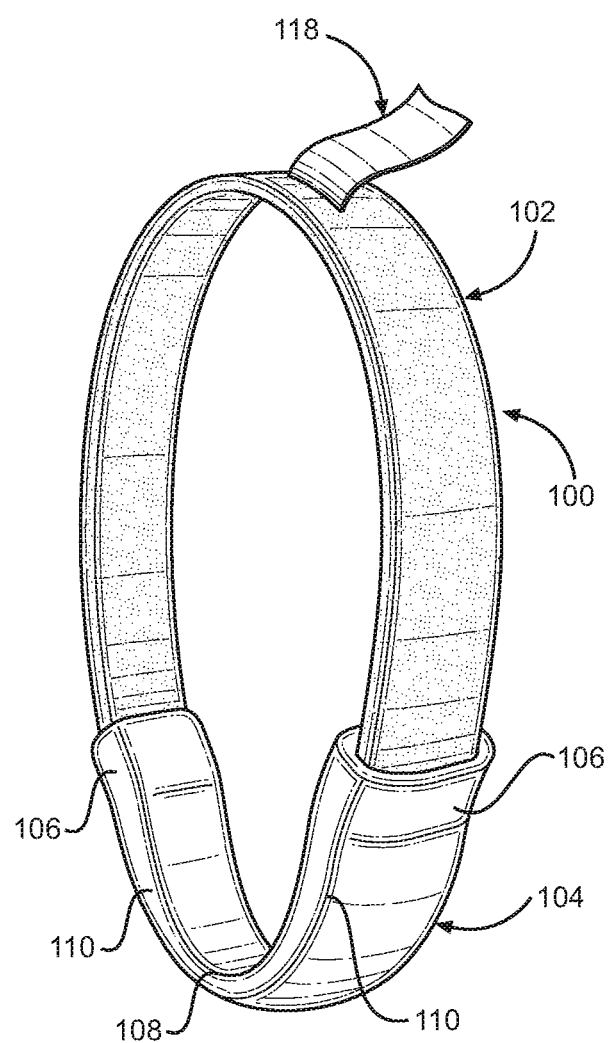
FIG. 1 is a perspective view of a prosthetic apparatus for treating erectile dysfunction having an expandable first member, a rigid or semi-rigid second member, and an installation flap.
Figure 2:
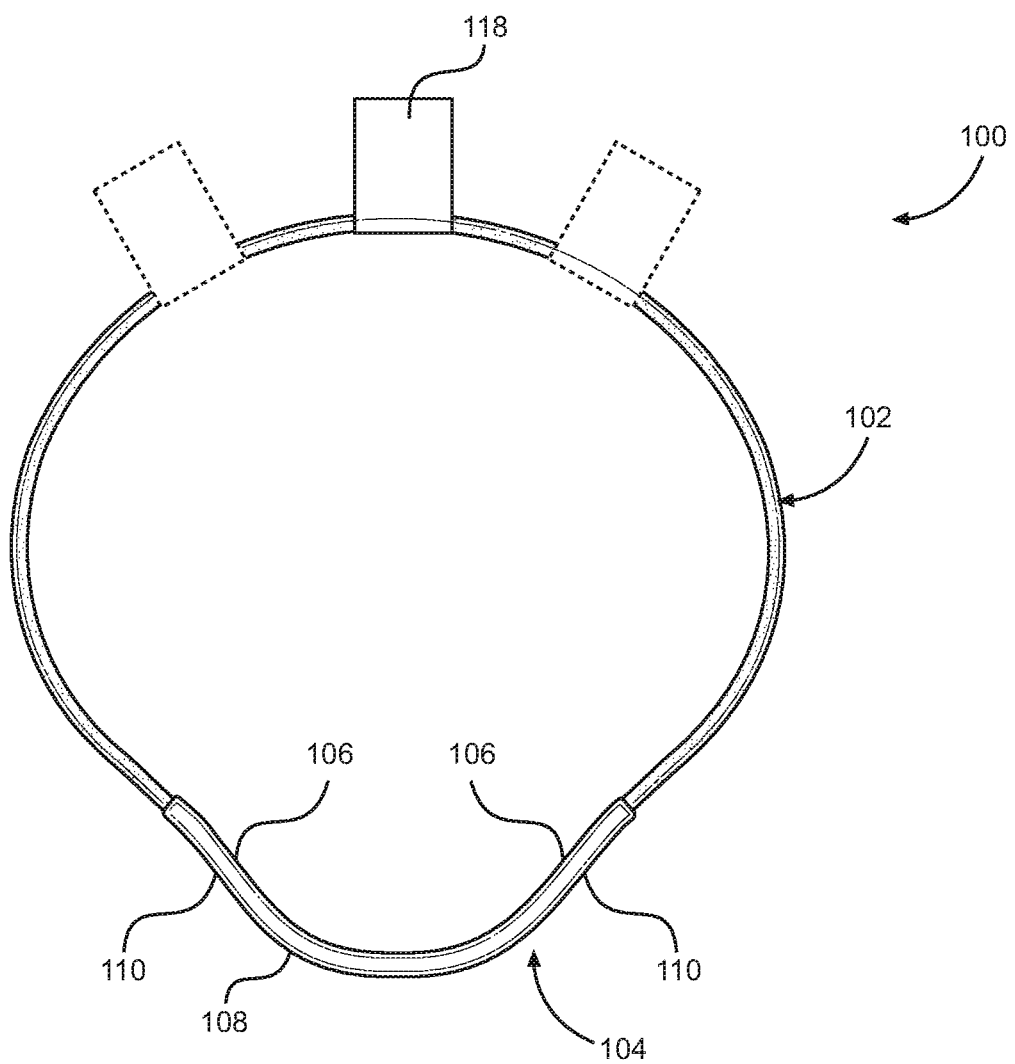
FIG. 2 is a front elevation view of the device of FIG. 1 and showing installation flaps at various optional locations.

Referring now to the drawings in which like reference characters designate like or corresponding characters throughout the several views, there is shown in FIGS. 1 and 2, a prosthetic apparatus 100 for enhancing erection of a penis. The apparatus 100 includes an expandable elastic upper member that encircles the male penis and compresses veins of the penis to reduce or eliminate venous flow of blood away from the penis, resulting in the achievement of and/or the maintaining of an erection. A rigid or semi-rigid lower member is attached to the elastic member and assists in avoiding constriction of the urethra. As the term is used herein, "rigid" means to maintain its approximate original dimension with minimal or no flexing when in use. On the other hand, "semi rigid" means to maintain its approximate dimension but with moderate flexing when in use. Among other things, avoiding constriction of the urethra can help to prevent retrograde ejaculation. Additionally, in contrast to prior devices, such as rigid penis rings, the apparatus 100 disclosed herein utilizes an expandable elastic band, which helps to eliminate the danger of necrosis of the penis by providing the user the ability of quickly removing the device, if needed.

Figure 3:
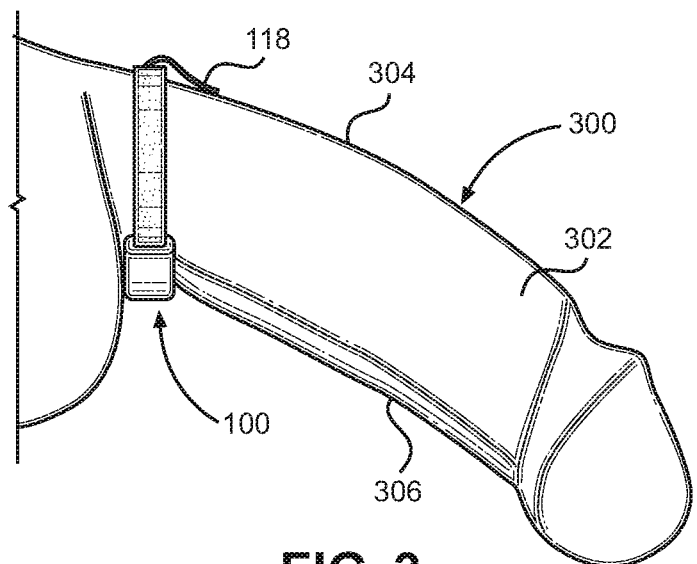
FIGS. 3 and 4 are side elevation and cross-sectional views depicting a prosthetic apparatus positioned outside the outer circumference of a partially flaccid male penis where veins within the penis are not constricted.
Figure 4:
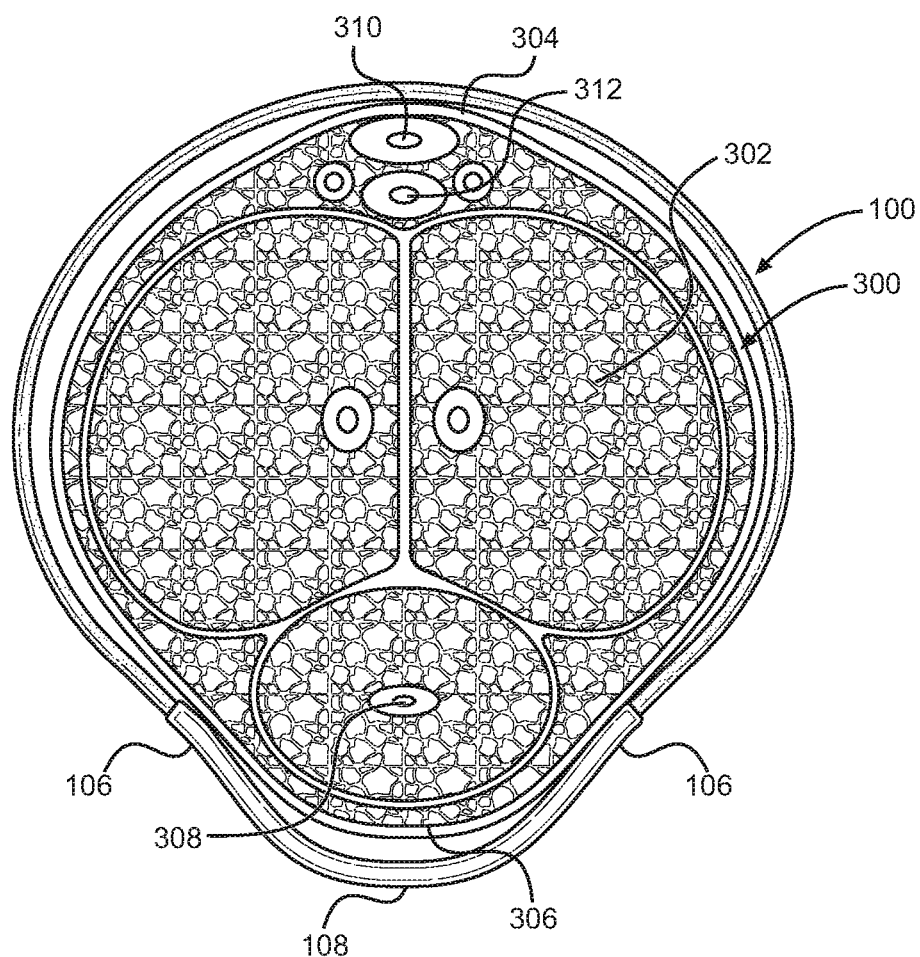

With reference to FIGS. 3 and 4, a typical penis 300 includes a shaft 302 having an upper portion 304 and a lower portion 306. A urethra 308 extends lengthwise along the lower portion of the shaft 302. A first vein 310, known as a superficial vein, for carrying blood away from the penis is located near the upper portion 304 of the shaft 302. A second vein 312, known as a deep dorsal vein, is located nearer the center of the shaft 302 between the first vein 310 and the lower portion 306. In this particular case, neither the first vein 310 nor the second vein 312 has been constricted. Accordingly, blood can freely flow into and out of the penis 300. FIGS. 3 and 4, therefore, depict the condition of a penis 300 before an apparatus 100 has been installed or after installation but while the penis remains substantially flaccid and without any constriction of the veins 310, 312.

Figure 5:
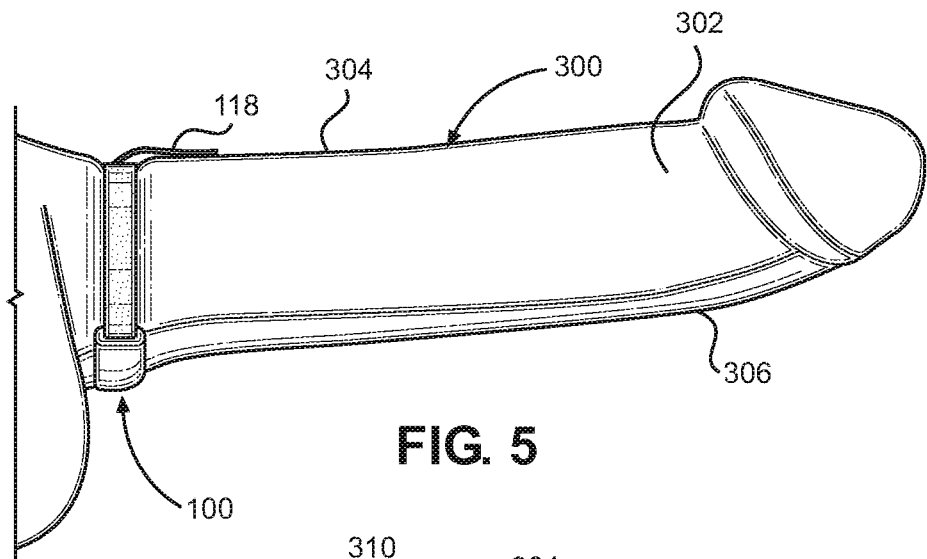
FIGS. 5 and 6 are side elevation and cross-sectional views depicting a prosthetic apparatus positioned within the outer circumference of an erect male penis where veins within the penis have been constricted.
Figure 6:
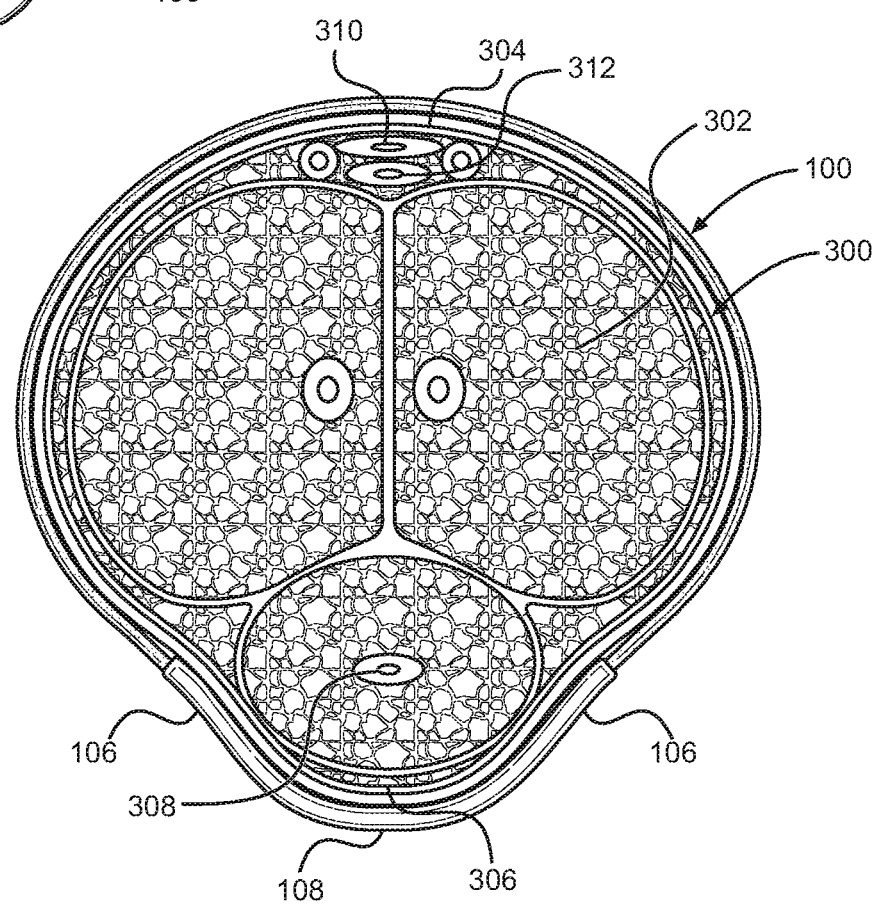

On the other, in FIGS. 5 and 6, the penis 300 has become erect. The apparatus 100 applies a force onto the penis 300 and that force has caused both of the veins 310, 312 to constrict. This constriction causes the volume of blood leaving the penis 300 to be reduced, which assists in maintaining and/or enhancing the erection. However, the device 100 is designed not to constrict and to avoid or substantially minimize pressure onto the urethra 308. Therefore, as shown best in FIG. 6, even when the veins 310, 312 are constricted, the urethra 308 is not. This allows the user to urinate and ejaculate even when the device is in place and also helps to prevent retrograde ejaculation (i.e., semen traveling incorrectly into the bladder instead of out of the body via the urethra).

The apparatus 100 shown in FIGS. 1 and 2 includes an expandable first member 102 that is mounted to a rigid or semi-rigid second member 104. The first member 102 is configured to at least partially encircle the upper portion 304 of the penis 300 and to apply pressure to partially constrict the first vein 310 to reduce the volume of blood carried away from the penis to maintain or enhance erection of the penis. In this particular case, the first member 102 fully encircles the upper portion 304 of the penis 300. The first member 102 may also be configured to, at the same time, partially constrict the second vein 312 to further reduce the volume of blood carried away from the penis to further enhance erection of the penis. This would depend on the amount of constriction force applied to the penis by the apparatus 100, which relies, in part, on the gauge and length of the expandable first member 102. As discussed further below, the first member 102 may be removed and replaced with a similar component that provides more or less constriction. Thus, the apparatus 100 is adjustable to provide more or less constriction, as desired or required.

The second member 104 is contoured and substantially conforms to the lower surface 306 of the penis 300. The second member 104 includes left and right shoulder 106 sections and a contoured section 108 that is formed between the shoulders 106. The contoured section 108 curves downwards to accommodate the lower portion of the penis. Transition sections 110, formed between the left and right shoulder sections 106 and the contoured section 108, may curve slightly inwards towards the penis 300 such that the second member 104 conforms to the lower portion 306 of the penis shaft 302. When properly installed, the device 100 is arranged so that shoulder sections 106 contact the penis shaft 302 adjacent either side of the urethra 308 and lower portion of the penis, including the urethra, is substantially located within the contoured section 108 and is not constricted when the device is in place.

Figure 7:
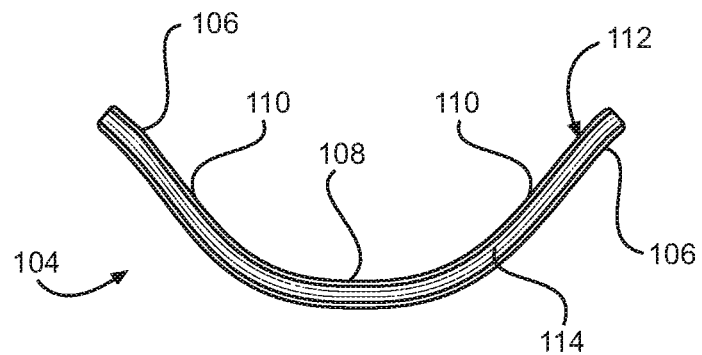
FIGS. 7 and 8 depict corresponding halves of a rigid second member having a tube construction.
Figure 8:
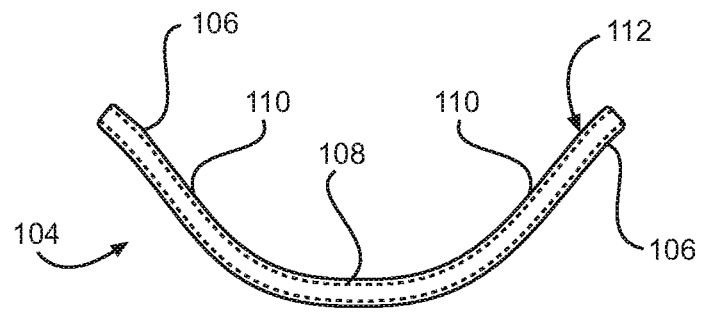

The lower member may be formed in a number of different ways that each provide different benefits, including lower cost of or ease of production, increased useful life, ease of repair, etc. For example, as shown in FIGS. 7 and 8, the second member 104 may be constructed from two corresponding half-tubes 112 that, when joined together, form a fully-enclosed tube. Each of the half tubes 112 includes a channel 114 that extends between the left and right shoulder sections 106, including through the transition section 110 and contoured sections 108, such that mounting the first half to the second half with the channels adjacent one another forms an enclosed tube configured to receive the first member. In certain embodiments, the entire enclosed tube has a circular, square, rectangular or oval-shaped cross section and a corresponding first member of the same type of cross section. In other embodiments, the first member may have cross sections different from the cross section of the second member. In certain embodiments, the first member may have any of a number of cross sections, including but not limited to, a sawtooth or wedge-shaped cross section. In other embodiments, only a portion of the enclosed tube, such as the contoured section 108 has a circular, square, rectangular or oval-shaped cross section.

Figure 9:
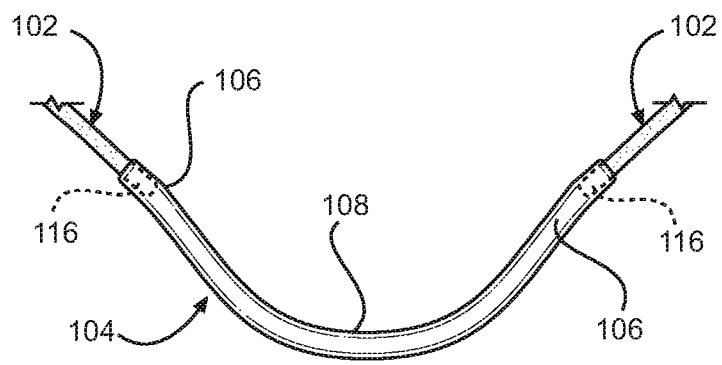
FIG. 9 depicts a rigid second member having insertion bores that receive ends of the expandable first member.

To connect the first member 102 to the second member 104, a portion of the first member may be inserted into the channel 114. In some embodiments, the first member 102 is a continuous one-piece ring, such as an O-ring, that is inserted into a first half tube and then a second half tube is placed over the first member and mounted to the first half tube. In other cases, ends of the first member 102 may be placed into the channel 114. With reference to FIG. 9, a solid tube with insertion bores 116 formed in either end may be used as an alternative to the half tube design discussed above. The insertion bores are located in the shoulder section 106 of the second member 104 and are configured to receive ends of the first member 102. In either case, an adhesive may be used to bond the two halves of the second member 104 together and to bond the first member 102 to the second member. Other well-known connection methods (e.g., friction fitting, crimping, hooks, etc.) may also be used mount portions of the first member 102 and second member 104 together.

The first member 102 is preferably constructed of a rubber, polymer, silicon, or other material that can expand, as needed, around the circumference of an erect penis and retract when the erection subsides. For example, an O-ring or other similar device may be used for the first member 102. The first member 102 may be provided in a range of sizes, including various lengths and thicknesses (i.e., gauge, cross section). The first member 102 may be lengthened or shortened during fabrication of the device in order to increase or decrease its diameter when placed into use. Additionally, the first member 102 may have larger or smaller cross sections. The length and thickness of the first member 102 may be adjusted during fabrication of the device in order to increase or decrease the amount of compression of the apparatus 100 on the user. The most successful ring to date has had a first member 102 having a thickness of 1.5 mm in diameter, but larger and smaller sizes may be utilized in order to provide differences in flexibility and pressure applied to the penis 300. On the other hand, the second member 104 may be constructed of metal, plastic, hard rubber or other sufficiently stiff material suitable for external bodily contact. Both the first member 102 and the second member 104 may be provided in a range of colors, including various skin tone colors and decorative colors. An advantage of a user selecting a color that closely approximates his skin tone, is that the device may be nearly undetectable when being worn.

Referring again to FIGS. 1 and 2, flexible installation flaps 118 may be attached to the first member 102 to assist in the installation, adjustment, or removal of the apparatus 100. The size, number, location, ornamentation or coloring of the flexible flaps may be adjusted to suit a user's preference, to improve functionality or ease of use of the device, improve comfort, reduce visibility, etc. The flaps 118 may be constructed from a number of materials, including, for example, rubber-based tape or other suitable flexible materials.

In use, the apparatus 100 is preferably sized so that constriction of the veins 310, 312 occurs only when an erection occurs. However, different users may require differently sized components to achieve an optimal fit. Accordingly, a sizing kit may be provided that includes instructions for user to correctly size the apparatus to their anatomy. This sizing kit may include measurement tools and multiple differently-sized components to allow the user to determine the size best suited to him. Accordingly, the kit may be provided with first and second members that have different lengths, thicknesses, and cross sections. This would enable a user to create a custom-fitted device that performs optimally for their anatomy and preference.

When fitted correctly, the apparatus 100 can be worn for extended periods of time, even for days or weeks at a time. Furthermore, it can stay in place over the flaccid penis due primarily to friction between the apparatus 100 and the user's skin, with little or no constriction of the veins 310, 312. As such, the device can be worn during normal activities and does not require removal when not in use like prior devices. Wearing the device 100 on a continual basis would enable a user to participate in sexual activity without the delay of waiting for the effects of a pill to take effect or to install another device.

The device 100 may be used in conjunction with erection enhancing drugs in order to further develop the erection of the user. This is especially useful if the user typically experiences venous leakage even when using such drugs, because the device 100 will suppress or eliminate such leakage.

The device 100 may be used in conjunction with a condom. While it may be fitted over a condom it is preferable to install the device 100 on the penis 300 first and then place the condom over it in order to minimize the possibility of rupturing the condom. An advantage of the device 100 is that it may be installed prior to engaging in sexual activity. However, in certain embodiments, the device 100 may be formed as an integral part of the condom such that the device and condom are simultaneously installed.

An additional advantage of the device 100 is that it is virtually undetectable to a user's partner when in use. As shown best in FIG. 5, with the exception of the optional installation flap 118, the device 100 is designed to sit at or below the user's skin level when in use. As such, the device does not protrude above the surface of the penis 300. Thus, the device is nearly undetectable, especially when the device 100 matches the user's skin color. In contrast, other penile constriction rings typically reside outside the outer circumference of the penis and are obvious to the user and his partner.

The foregoing description of preferred embodiments for this disclosure have been presented for purposes of illustration and description. They are not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the device disclosed in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A prosthetic apparatus for enhancing penile erection of a penis, where the penis includes a shaft with an upper portion and a lower portion, a urethra extending lengthwise along the lower portion of the shaft, and a first vein for carrying blood away from the penis located between the upper and lower portions, the apparatus comprising:
   an expandable first member configured to at least partially encircle the upper portion of the penis and to partially constrict the first vein to reduce the volume of blood carried away from the penis via the first vein in order to enhance erection of the penis; and
   a second member mounted to the first member and configured to contact a lower portion of the penis, the second member having:
      left and right shoulder sections configured to contact the penis shaft along the left and right sides the urethra; and
      a contoured section curving between the shoulder sections so that, when the shoulder sections contact the penis shaft and the first member at least partially encircles the upper portion of the penis, the contoured section extends around and does not constrict the urethra.

2. The apparatus of claim 1 wherein the first member comprises opposing ends that are fixedly mounted to the left and right shoulder sections of the second member.

3. The apparatus of claim 2 further comprising insertion bores formed in ends of the second member proximate the shoulder sections that are configured to receive ends of the first member.

4. The apparatus of claim 1 wherein the first member is a continuous ring and the second member comprises a connection member for receiving and securely holding a portion of the first member.

5. The apparatus of claim 4 wherein the connection member comprises a channel that extends between the left and right shoulder sections, including through the contoured section, which is configured to receive and securely hold a portion of the first member.

6. The apparatus of claim 1 wherein the second member comprises a first half tube and a second half tube, each half tube having a channel that extends between the left and right shoulder sections, including through the contoured section, such that mounting the first half tube to the second half tube with the channels adjacent one another forms a fully-enclosed tube configured to receive the first member.

7. The apparatus of claim 6 wherein the first and second half tubes are adhesively bonded or mechanically fastened together with at least a portion of the first member located in the enclosed tube.

8. The apparatus of claim 1 wherein at least a portion of the second member has a cross section having a shape selected from the group consisting of a circle, square, rectangle, and oval.

9. The apparatus of claim 1 wherein at least a portion of the first member has a cross section having a shape selected from the group consisting of a circle, square, rectangle, and oval.

10. The apparatus of claim 1 wherein the first and second members are sized such that they lie entirely within the outer circumference of the penis shaft of an erect penis such that the apparatus does not extend beyond the outer circumference of the erect penis.

11. The apparatus of claim 1 further comprising an installation flap mounted to the first portion that is sized to be grasped and pulled by a user to facilitate installation, adjustment, and removal of the apparatus.

12. The apparatus of claim 11 wherein the installation flap is flexible.

13. The apparatus of claim 11 wherein the installation flap is located at the center of the first portion such that it is positioned at the center of the upper portion when the apparatus is placed onto the penis.

14. The apparatus of claim 11 comprising two installation flaps mounted to the first portion that are sized to be grasped and pulled by a user to facilitate installation and removal of the apparatus.

15. The apparatus of claim 11 wherein the installation flap is positioned along the left or right side of the penis when the apparatus is placed onto the penis.

16. The apparatus of claim 1 wherein the second portion is rigid.

17. The apparatus of claim 1 wherein the second portion is semi-rigid.

18. The apparatus of claim 1 further comprising transition sections formed between the left and right shoulder sections and the contoured section that curve inwards towards the penis such that the second member is shaped to conform to the lower portion of the shaft.

19. A prosthetic apparatus kit for enhancing penile erection of a penis, where the penis includes a shaft with an upper portion and a lower portion, a urethra extending lengthwise along the lower portion of the shaft, and a first vein for carrying blood away from the penis located between the upper and lower portions, the kit comprising:
 a plurality of expandable first members of varying sizes, each first member configured to at least partially encircle the upper portion of the penis and to partially constrict the first vein to reduce the volume of blood carried away from the penis via the first vein in order to enhance erection of the penis; and
 a plurality of second members of varying sizes, each second member configured to mount to one of the first members and configured to contact a lower portion of the penis and having:
  left and right shoulder sections configured to contact the penis shaft along the left and right sides the urethra; and
  a contoured section formed between and extending outwards away from the shoulders so that, when the shoulder sections contact the penis shaft and the first member at least partially encircles the upper portion of the penis, the contoured section extends over and does not constrict the urethra,
 wherein a user may create a custom-fitted device using various combinations of the first and second members that is sized for and performs optimally for the user's anatomy and preference.

20. The apparatus of claim 1 wherein said first vein is a superficial vein and the penis further includes a second deep tissue dorsal vein and wherein the first and second members are sized so that, when the apparatus is positioned onto the shaft of the penis, the first member at least partially constricts both the first and second veins to reduce the volume of blood carried away from the penis in order to enhance erection of the penis.

\* \* \* \* \*